United States Patent [19]
Jenkins

[11] 3,948,246
[45] Apr. 6, 1976

[54] HEATER FOR SPORTS BENCHES
[76] Inventor: John F. Jenkins, 137 N. Shore Road, Absecon, N.J. 08201
[22] Filed: July 17, 1974
[21] Appl. No.: 489,170

[52] U.S. Cl. .............. 126/204; 126/208; 98/2.03; 219/217; 237/77; 297/180
[51] Int. Cl.² .......................................... A61F 7/06
[58] Field of Search .......... 4/164, 165; 237/77, 50; 126/204, 205, 206, 208; 297/180; 219/217; 239/553.3; 5/332; 98/2.03

[56] References Cited
UNITED STATES PATENTS

| 1,091,253 | 3/1914 | Stockstrom et al. | 239/553.3 |
| 2,567,323 | 9/1951 | Cyphert | 126/208 |
| 2,590,026 | 3/1952 | Marx | 126/205 |
| 2,782,834 | 2/1957 | Vigo | 297/180 |
| 2,829,635 | 4/1958 | Teller | 126/208 |
| 2,851,573 | 9/1958 | Muccilli | 126/204 |

FOREIGN PATENTS OR APPLICATIONS

| 440,895 | 2/1927 | Germany | 126/208 |

Primary Examiner—Carroll B. Dority, Jr.
Assistant Examiner—Larry I. Schwartz
Attorney, Agent, or Firm—Jackson, Jackson & Chovanes

[57] ABSTRACT

The invention concerns heaters, particularly for sports benches and more especially for the benches on which substitute players of the team sit during games. In the preferred form, a self-contained heater such as a combustion operated construction heater with blower produces the heat behind the bench, and the heat is conducted through a conduit into the space beneath the bench, and then through a T-conduit in either direction to points from which it is distributed. The space beneath the bench confines the heat on the front, back, sides and bottom. Heat is distributed through openings in the top of the bench toward the back, and also through openings in the front of the bench, which may be at the top of the front of the bench and at the bottom of the bench. In a less preferred embodiment, heaters may be in spaces continuous with the bench. An option available is that a space behind the bench is provided in which the toes can be inserted, and flexible tubes are provided at the end of the bench, so that heat may be conducted either to the space around the neck of an athlete or the like.

3 Claims, 5 Drawing Figures

HEATER FOR SPORTS BENCHES

DESCRIPTION OF THE INVENTION

The invention concerns heaters for benches, particularly benches on which athletes or the like may sit, such as substitute players waiting to go in the game.

In the preferred embodiment, the heat is developed by a self-contained heater provided with a blower, such as a construction heater which is desirably placed behind the bench. The heat developed is then conducted by a conduit, desirably a 9 inch conduit, into the space under the bench, from which it is carried through a T in the conduit to discharge at two points into the space below the bench.

The space below the bench is substantially closed on the bottom, front, back and sides, except for distribution openings by which the heat is distributed to personnel in and around the bench. These distribution openings are on the top toward the back of the bench, and also in the front of the bench, such as the top of the front of the bench and the bottom of the front of the bench.

Some of the athletes sitting on the bench may have trouble through failure to heat their toes, and for this purpose openings into the interior of the bench are provided at the lower level in the back of the bench. Also pliable tubes are provided to conduct heat, for example to the neck, face and head of the user.

These openings desirably have covers and may be optionally opened.

In adapting the invention to use on the benches in tiers, the source of heat is distributed continuously with the benches at intervals along them.

The drawings bring out the invention by exemplified embodiments.

Figure 1:
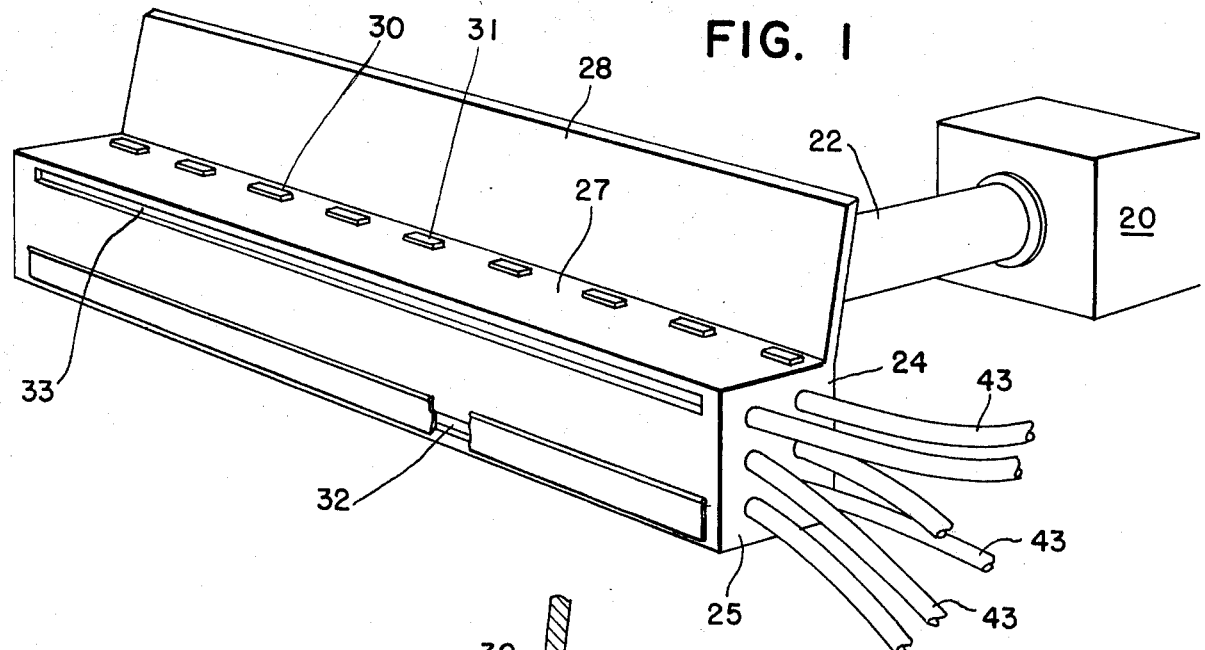
FIG. 1 is a perspective of a bench, heater and connecting conduit.
Figure 2:
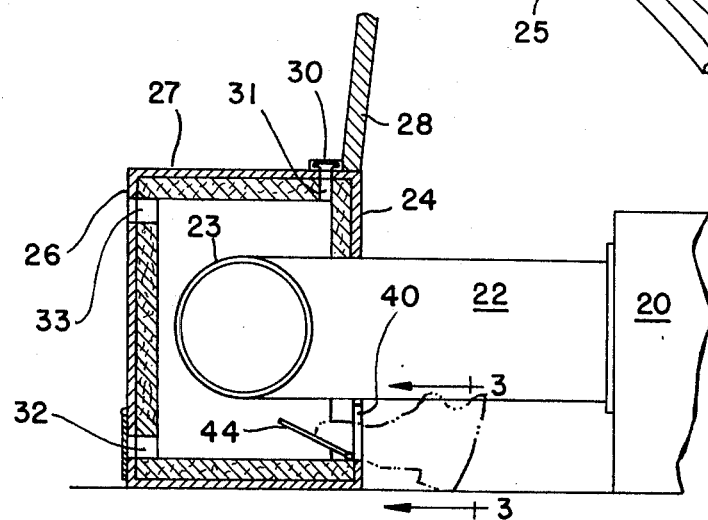
FIG. 2 is a section through the bench conduit and heater.
Figure 3:
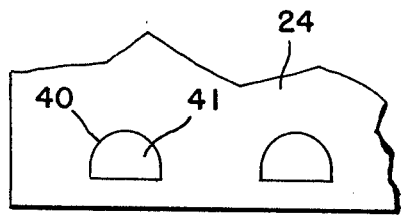
FIG. 3 is a fragmentary back view of the bench.
Figure 4:
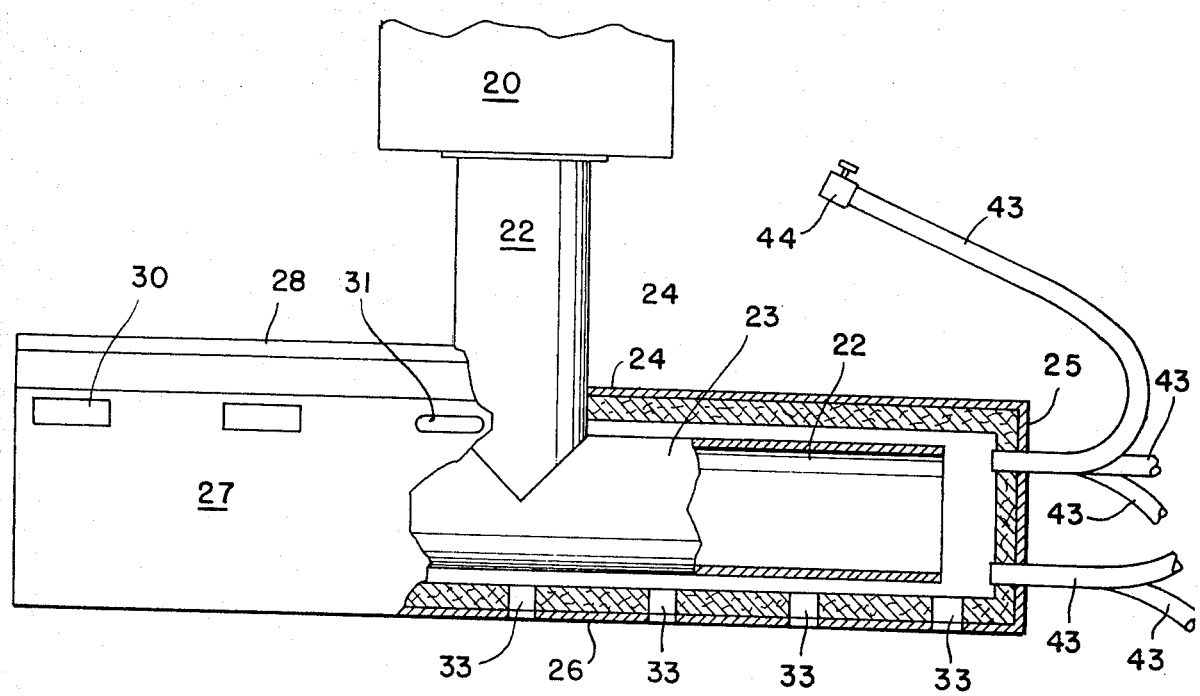
FIG. 4 is a top plan view partly in section.
Figure 5:
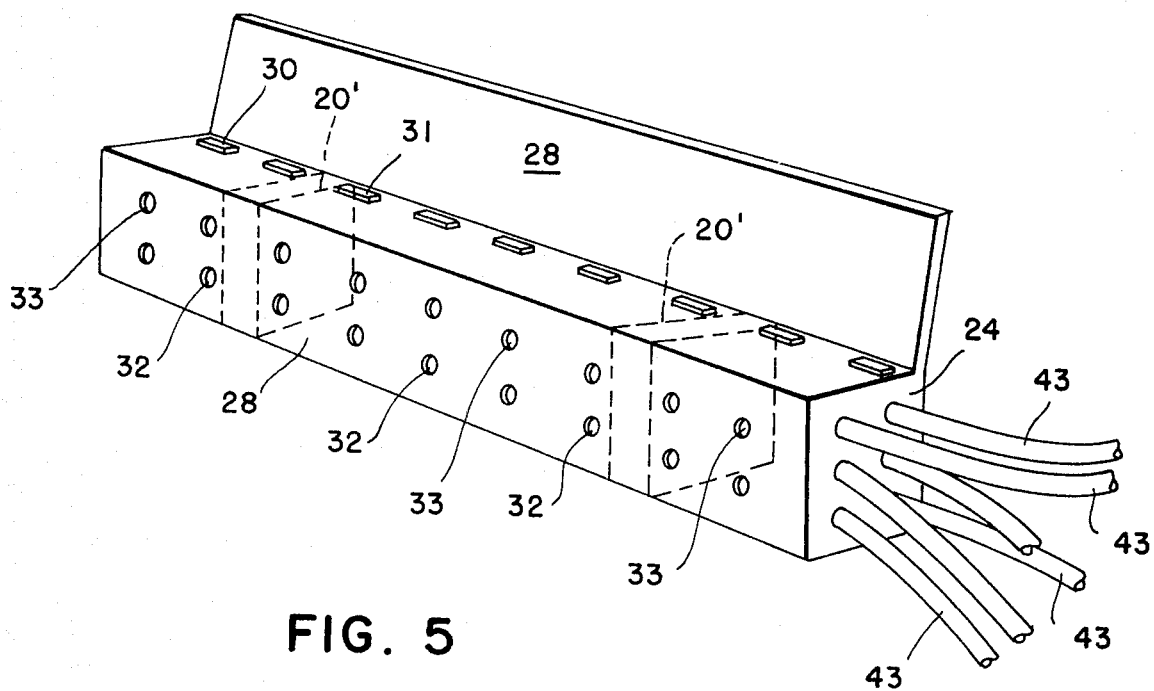
FIG. 5 is a plan section of an alternate form.

FIG. 1 shows a bench of the type used by athletes while waiting for substitutes. The bench is preferably about one foot and a half high, 10 inches or so deep and about 15 feet long, although of course the specific requirements will be varied. It may have a back rest. The part that the athlete sits on may be made of wooden planks, say 2 inches or so thick, while the front, back and sides of the lower part are preferably formed of plywood joined in the form of a box, which rests on the ground or concrete and is preferably bottomless. The lower part may be made of plywood of ½ inch or thicker and the backrest may be of plywood such as one inch plywood.

The means of generating the heat is preferably by combustion, although it may be generated by electric resistance heating. Well known units for generating heat are the self-contained combustion heaters which contain a burner and also a blower and which produce a blast of warmed air through for example a 9 inch conduit.

These heaters have substantially 100 percent combustion and may be used in spaces requiring heat, such as warehouses and construction shacks.

In the preferred form a combustion heater 20 is used having a blower which produces heated air under pressure blown through a conduit 22 into a T conduit 23 under the bench.

The bench has a back 24, two ends 25, a front 26, and a top 27. It has an optional back rest 28.

At the back of the top of the bench, there are slots 30, which are covered with closures 31, preferably of the sliding type. In the front of the bench there are a slot 33, preferably about the front corner and a slot 32 at the bottom of the front, preferably provided with a removable cover.

In an optional form, such as is suited to benches in tiers which must be heated, the heaters 20' are arranged continuously with the benches at intervals along the benches, and they discharge at intervals under the benches corresponding to the intervals at which the T-conduit discharges.

In wearing football shoes, the toes of the wearer may be susceptible of becoming cold and the wearer may want therefore a place to warm his toes. Openings 40 are provided covered by flaps 41 in the back of the bench, so that athletes or others could insert the tips of the shoes in the holes. This is spring loaded and preferably a flop hinge.

At times the athletes or others may desire to have the neck, face or head heated and for this purpose flexible tubes 43 are made available, cut off by valves 44. This may also be used to warm the hands, particularly of a substitute player who may have to throw a pass or catch a pass if he is put in the football game.

While the use by football teams is particularly pleasing, the invention may also find use, for example, for spectators of parades, such as the Philadelphia Mummer's Parade and especially for broadcasters who are broadcasting such parades.

It will be evident of course that on the conduits and the like which convey heat, insulation may be useful or even essential.

In view of my invention and disclosure, variations and modifications to meet individual whim or particular need will doubtless become evident to others skilled in the art, to obtain all or part of the benefits of my invention without copying the device shown, and I therefore claim all such insofar as they fall within the reasonable spirit and scope of my claims.

Having thus described my invention, what I claim as new and desire to secure by Letters Patent is:

1. In a heater for benches for use in outdoor sports events, a self-contained heating means, external to the bench, a bench having back, front, sides and substantially unyielding top, thus producing a closed under-bench space, a conduit for heated air from the heater to the bench, a cross conduit for heated air under the bench for distribution of heat in both directions, and perforations in both the upper and lower part of the front of the bench and in the bench top for distribution of heated air from under the bench.

2. A heater for benches for outdoor use, comprising a bench having sides, front, top and back, a heater external to the space, a conduit connecting the heat to the space, a T-shaped cross connection from the conduit for distributing the heat within the space, slots in the back portion of the top of the seat for distributing the heat on the back of the person sitting down, and openings in both the top and bottom of the front of the bench for distributing the heat to the person sitting on the bench approximately at the top and the bottom of the front.

3. In a heater for benches for outdoor use, a bench having a closed space beneath it with sides, front, back and top, a self-contained heater, a conduit to pass the heat from the heater to the space beneath the bench, a cross connection from the conduit within the space for distributing the heat to the space, openings in the back of the seat for allowing the heat to go up the back of the person sitting on the bench, openings in both the top and bottom of the front of the bench for distributing the heat to the legs of the person sitting on the bench, a pliable conduit for conducting heat from the end of the bench to a person standing near the bench and openings in the back of the bench for warming the toes of the person standing behind the bench.

* * * * *